United States Patent [19]

Lin et al.

[11] Patent Number: 5,508,418
[45] Date of Patent: Apr. 16, 1996

[54] INTERMEDIATES FOR THE PREPARATION OF ENANTIOMERICALLY-PURE-3-METHYL-5-(1-C1-C3-ALKYL)-2-PYRROLIDINYL) ISOXAZOLE

[75] Inventors: Nan-Horng Lin, Mundelein; Yun He, Zion; William H. Bunnelle, Mundelein, all of Ill.

[73] Assignee: Abbott Laboratories, Abbott Park, Ill.

[21] Appl. No.: 477,057

[22] Filed: Jun. 7, 1995

Related U.S. Application Data

[63] Continuation-in-part of Ser. No. 234,442, Apr. 28, 1994, Pat. No. 5,424,444, which is a continuation-in-part of Ser. No. 117,819, Sep. 8, 1993, abandoned.

[51] Int. Cl.$^6$ .................. C07D 207/06; C07D 261/04; C07D 261/06

[52] U.S. Cl. .................. 548/243; 548/247; 548/566
[58] Field of Search ................. 548/243, 247, 548/566

[56] References Cited

PUBLICATIONS

CA 123:55872 Isoxazole, ... function. Garvey et al., 1995.

*Primary Examiner*—Joseph K. McKane
*Attorney, Agent, or Firm*—Jerry F. Janssen; Richard A. Elder

[57] ABSTRACT

Novel compounds useful in the preparation of enantiomerically-pure 3-methyl-5-(1-($C_1$–$C_3$-alkyl)-2-pyrrolidinyl) isoxazole in high yield, namely 5(S)-(3-methyl-5-isoxazolyl)-2-pyrrolidinone, 3-methyl-5-(1-methyl-2-pyrrolidinyl)-5-hydroxy-4,5-dihydro-isoxazole, and 1-(1-methyl-2(S)-pyrrolidinyl)-1,3-butanedione-3-oxime.

1 Claim, No Drawings

INTERMEDIATES FOR THE PREPARATION OF ENANTIOMERICALLY-PURE-3-METHYL-5-(1-C1-C3-ALKYL)-2-PYRROLIDINYL)ISOXAZOLE

This application is a continuation-in-part of allowed U.S. patent application Ser. No. 08/234,442, filed Apr. 28, 1994, now U.S. Pat. No. 5,424,444 which is a continuation-in-part of U.S. patent application Ser. No. 08/117,819, filed Sep. 8, 1993, now abandoned.

TECHNICAL FIELD

This invention relates to a process for preparing pyrrolidinyl isoxazoles, particularly to a method of preparing 3-methyl-5-(1-($C_1$-$C_3$-alkyl)-2(S)-pyrrolidinyl) isoxazole, more particularly 3-methyl-5-(1-methyl-2(S)-pyrrolidinyl)isoxazole, that affords a high yield of enantiomerically-pure product. These compounds and pharmaceutical compositions thereof are cholinergic ligands, selective for neuronal nicotinic receptors, that are useful in treating various cognitive, neurological and mental disorders, such as dementias and anxiety, which are characterized by decreased cholinergic function, or in treating or preventing withdrawal symptoms caused by the cessation of chronic or long term use of tobacco products, as well as ameliorating the symptoms of anxiety and frustration associated with withdrawal of other addictive substances such as, for example, cocaine, diazepam or alcohol, and in treating alcohol intoxication and petit mal absence epilepsy.

BACKGROUND OF THE INVENTION

The central nervous system disorders that may be treated by novel isoxazole compounds, particularly 3-methyl-5-(1-methyl-2-pyrrolidinyl)isoxazole, have been described in U.S. patent application, Ser. No. 08/118,079, filed Sep. 8, 1993, which is incorporated herein by reference. That Application teaches that a 2-oxopyrrolidine carboxylic acid ester (compound 21 of Scheme IV therein) may be condensed with a dianion of acetone oxime only when the pyrrolidine ring nitrogen substituent ($R^5$ therein) is a $C_1$-$C_4$-alkyl group, and not when it is hydrogen. Further, said Application teaches (Example 22c) that the condensation reaction generates a racemic product. Also, the reported cyclization of a betaketo oxime, wherein the oxime group is a functional group on a fused ring system and the product contains a fused oxazolidine ring (British Patent No. 1,354,097 and published German Application DE2166685) cannot be said to teach or suggest that cyclization with non-fused ring starting materials is possible or would result in an enantiomerically-pure product.

It has now been found that an enantiomerically-pure product may be obtained in a process wherein an alkyl ester of N-alkyl-L-proline, particularly N-methyl-L-proline, is converted into a compound having a keto-oxime grouping in an extended side-chain, which is then cyclized and dehydrated, and in an alternate process wherein an alkyl ester of L-pyroglutamic acid is converted into a compound having a keto-oxime grouping in an extended side-chain, which is cyclized and dehydrated, then N-alkylated, and more specifically N-methylated.

SUMMARY OF THE INVENTION

This invention is directed to a novel, high yield process for preparing enantiomerically-pure 3-methyl-5-(1-($C_1$-$C_3$-alkyl)-2-pyrrolidinyl)isoxazole, particularly enantiomerically-pure 3-methyl-5-(1-methyl-2-pyrrolidinyl)isoxazole, according to which a suitably-protected pyrrolidine or 2-oxopyrrolidine, is converted into a compound having a keto-oxime grouping, and a resulting beta-keto oxime intermediate (1-(1-($C_1$-$C_3$-alkyl)-5-oxo-2(S)-pyrrolidinyl))-1,3-butanedione-3-oxime or 1-(1-($C_1$-$C_3$-alkyl)-2(S)-pyrrolidinyl)-1,3-butanedione-3-oxime or the cyclic ketal of the latter, 3-methyl-5-(1-($C_1$-$C_3$-alkyl)- 2-pyrrolidinyl)-5-hydroxy-4,5-dihydro-isoxazole) is cyclized into an isoxazole product by dehydration.

DETAILED DESCRIPTION OF THE INVENTION

This invention relates to a novel process for preparing in high yield the enantiomerically-pure 3-methyl-5-(1-($C_1$-$C_3$-alkyl)-2-pyrrolidinyl)isoxazole of formula (1),

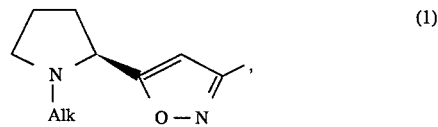

wherein Alk is $C_1$-$C_3$-alkyl, comprising:
(a) treating an N-Alk-L-proline ester compound of formula (2),

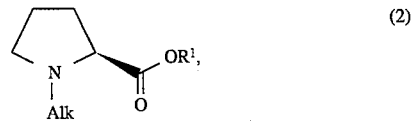

wherein Alk is $C_1$-$C_3$-alkyl,
with suitable reagents, including, but not limited to, an excess of a salt of a dianion of acetone oxime; an anion of acetonitrile followed by a methyl Grignard reagent and subsequent reaction of the intermediate with hydroxylamine; or an anion of an imine of acetone with subsequent reaction of the intermediate with hydroxylamine;
with or without isolating the novel reaction product of formula (3),

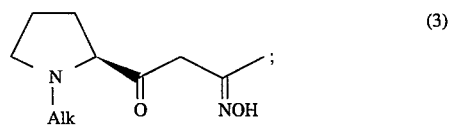

then
(b) reacting the reaction product of step (a), the compound of formula (3), with a cyclizing and dehydrating reagent, as defined below, in a suitable solvent, at a temperature of from 0° C. to reflux temperature for from 3-to-48 hours, and isolating the desired product, in high chiral purity.

It should be understood that the compound of formula (3) may further autocyclize to form an novel intermediate compound of formula (4):

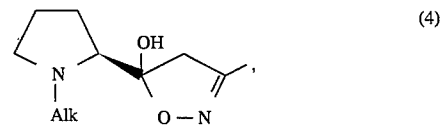

which may then undergo dehydration in the presence of a cyclizing and dehydrating reagent to give the final product of formula (1); and it will be appreciated by those skilled in the art that compounds (3) and (4) may be in equilibrium with each other, in solution or in crude isolates of (3), and that the actual position of equilibrium is not important in the process of the invention.

The starting material of formula (2) may be prepared by standard methods known to those skilled in the art, by first forming the appropriate alkyl ester of L-proline, then N-alkylating the ester compound. Alternately, of course, it is possible to prepare the starting material of formula (2) by alkylation of L-proline to give the N-alkyl-L-proline, and then preparing the appropriate alkyl ester thereof.

It will be obvious to one skilled in the art that the Alk group in compound (2) may be replaced with an R group, which is a protecting group, such as benzyloxycarbonyl, tert-butyloxycarbonyl, methoxycarbonyl, or formyl, for example. Such a starting material may be carried through steps (a) and (b) of the process described above, to give a compound similar to that of formula (1), wherein the Alk is replaced with R. Subsequently, the protecting group may be removed and the Alk group added to give the desired compound of formula (1). Such an extension of the process is to be considered within the scope of the present invention.

One embodiment of the process for preparing compound (1), comprises:

(a) reacting the compound of formula (2), wherein Alk is $C_1$–$C_3$-alkyl, with an excess of a salt of the dianion of acetone oxime in a solution of THF, at a temperature of from −10° C. to ambient, vigorously mixing of the reagents, and optionally isolating the novel compound of formula (3),

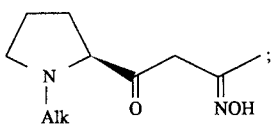

(3)

then (b) reacting the compound of formula (3) with sulfuric acid as the cyclizing and dehydrating reagent in a suitable solvent, at a temperature from 0° C. to reflux temperature for from 3-to-48 hours, and isolating the desired product, in high chiral purity.

A preferred embodiment is the process for preparing the compound of formula (1), wherein Alk is methyl, comprising:

(a) reacting the compound of formula (2), wherein Alk is methyl, with an excess of the mixed Na/Li salt of the dianion of acetone oxime in a solution of THF:hexane, at a temperature of from −10° C. to ambient, with simultaneous addition and vigorous mixing of the reagents, without isolating the reaction product of formula (3a),

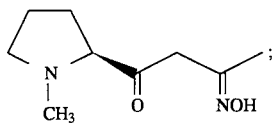

(3a)

then (b) reacting the reaction product of formula (3a) with the cyclizing and dehydrating reagent sulfuric acid in a THF/$H_2O$ mixture, at a temperature from 0° C. to reflux temperature for from 3-to-48 hours, and isolating the desired product, in high chiral purity.

A more preferred embodiment is the process for preparing the compound of formula (1), wherein Alk is methyl, comprising:

(a) reacting the compound of formula (2), wherein Alk and $R^1$ are methyl, with an excess of the mixed Na/Li salt of the dianion of acetone oxime in a solution of THF:hexane, at a temperature of from −10° C. to ambient, with simultaneous, addition and vigorous mixing of the reagents, without isolating the reaction product of formula (3a),

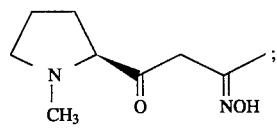

(3a)

then (b) reacting the reaction product of formula (3a) with the cyclizing and dehydrating reagent sulfuric acid in a THF/$H_2O$ mixture, at a temperature from 0° C. to reflux temperature for from 3-to-48 hours, and isolating the desired product, 3-methyl-5-(1-methyl-2-pyrrolidinyl)isoxazole, in high chiral purity.

Another embodiment of the process for preparing compound (1), comprises:

(a) reacting the compound of formula (2), wherein Alk is $C_1$–$C_3$-alkyl, with an anion of acetonitrile followed by a methyl Grignard reagent and subsequent reaction of the intermediate with hydroxylamine, with or without isolating the novel reaction product of formula (3),

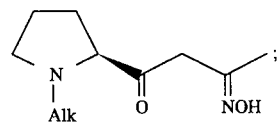

(3)

then (b) reacting the reaction product of step (a), the compound of formula (3), with a cyclizing and dehydrating reagent, as defined below, in a suitable solvent, at a temperature of from 0° C. to reflux temperature for from 3-to-48 hours, and isolating the desired product, in high chiral purity.

Another preferred embodiment is the process for preparing the compound of formula (1), wherein Alk is methyl, comprising:

(a) reacting the compound of formula (2), wherein Alk is methyl, with an anion of acetonitrile followed by a methyl Grignard reagent and subsequent reaction of the intermediate with hydroxylamine, with or without isolating the novel reaction product of formula (3a),

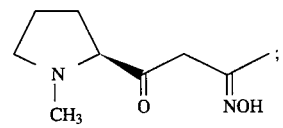

(3a)

then (b) reacting the reaction product of step (a), the compound of formula (3a), with a cyclizing and dehydrating reagent, as defined below, in a suitable solvent, at a temperature of from 0° C. to reflux temperature for from 3-to-48 hours, and isolating the desired product, in high chiral purity.

Another more preferred embodiment is the process for preparing the compound of formula (1), wherein Alk is methyl, comprising:

(a) reacting the compound of formula (2), wherein Alk and $R^1$ are methyl, with an anion of acetonitrile followed by a methyl Grignard reagent and subsequent reaction of the intermediate with hydroxylamine, with or without isolating the novel reaction product of formula (3a),

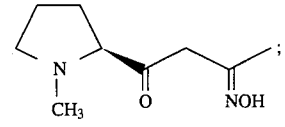

(3a)

then (b) reacting the reaction product of step (c), the compound of formula (3a), with a cyclizing and dehydrating reagent, as defined below, in a suitable solvent, at a temperature of from 0° C. to reflux temperature for from 3-to-48 hours, and isolating the desired product, 3-methyl-5-(1-methyl-2-pyrrolidinyl)isoxazole, in high chiral purity.

A further embodiment of the process for preparing compound (1), comprises:

(a) reacting the compound of formula (2), wherein Alk is $C_1$–$C_3$-alkyl, with an anion of an anion of an imine of acetone and subsequent reaction of the intermediate with hydroxylamine, with or without isolating the novel reaction product of formula (3),

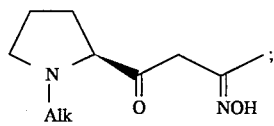
(3)

then (b) reacting the reaction product of step (a), the compound of formula (3), with a cyclizing and dehydrating reagent, as defined below, in a suitable solvent, at a temperature of from 0° C. to reflux temperature for from 3-to-48 hours, and isolating the desired product, in high chiral purity.

A further preferred embodiment is the process for preparing the compound of formula (1), wherein Alk is methyl, comprising:

(a) reacting the compound of formula (2), wherein Alk is methyl, with an anion of anion of an imine of acetone, wherein the imine may be 1-methylethylicline-cyclohexylamine or 1-methylethylidineisopropylamine and subsequent reaction of the intermediate with hydroxylamine, with or without isolating the novel reaction product of formula (3a),

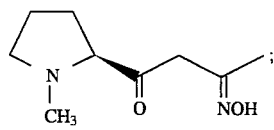
(3a)

then (b) reacting the reaction product of step (a), the compound of formula (3a), with a cyclizing and dehydrating reagent, as defined below, in a suitable solvent, at a temperature of from 0° C. to reflux temperature for from 3-to-48 hours, and isolating the desired product, in high chiral purity.

A further more preferred embodiment is the process for preparing the compound of formula (1), wherein Alk is methyl, comprising:

(a) reacting the compound of formula (2), wherein Alk and $R^1$ are methyl, with an anion of 1-methylethylidineisopropylamine and subsequent reaction of the intermediate with hydroxylamine, with or without isolating the novel reaction product of formula (3a),

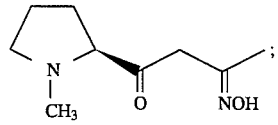
(3a)

then (b) reacting the reaction product of step (a), the compound of formula (3a), with a cyclizing and dehydrating reagent, as defined below, in a suitable solvent, at a temperature of from 0° C. to reflux temperature for from 3-to-48 hours, and isolating the desired product, 3-methyl-5-(1-methyl-2-pyrrolidinyl)isoxazole, in high chiral purity.

Alternately, the desired 3-methyl-5-(1-($C_1$–$C_3$-alkyl)-2(S)-pyrrolidinyl)isoxazole compound of formula (1) may be prepared in high yield by a novel process comprising:

(a) reacting a starting material, (S)-pyroglutamic acid, of formula (5),

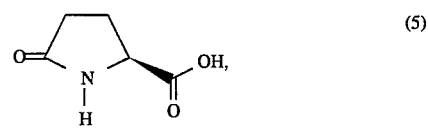
(5)

with an esterifying reagent at from –10° C. to 80° C. for from 3-to-48 hours, to prepare the (S)-pyroglutamic acid ester of formula (6),

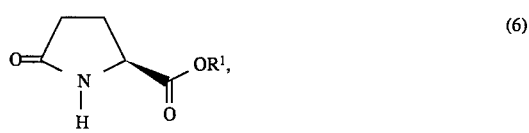
(6)

wherein $R^1$ is methyl or ethyl;

(b) reacting the compound of formula (6) with an excess of a salt of the dianion of acetone oxime in a suitable solvent, at a temperature of from –30° C. to ambient temperature, with vigorous mixing of the reagents, to form the intermediate product, 1-(1-methyl-5-oxo-2(S)-pyrrolidinyl)-1,3-butanedione-3-oxime, which is not isolated, but which is cyclized and dehydrated by reaction with a strong acid at ambient-to-reflux temperature for from 0.5 - to - 3 hours, to produce the novel 5(S)-(3-methyl-5-isoxazolyl)-2-pyrrolidinone compound of formula (7),

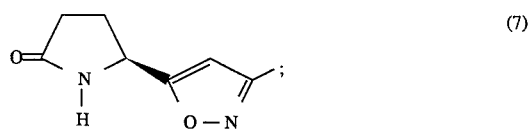
(7)

(c) reducing the compound of formula (7) with a reducing agent known to reduce lactams to cyclic amines, particularly an agent selected from the group consisting of lithium aluminum hydride, $NaBH_4/BF_3$, $NaBH_4/CH_3SO_3H$, $NaBH_4$/camphor sulfonic acid, borane/dimethyl sulfide and borane/THF, to give the 3-methyl-5-(2(S)-pyrrolidinyl)isoxazole compound of formula (8),

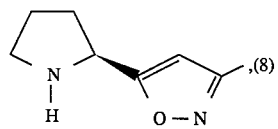
,(8)

which may or may not be isolated; then (d) N-alkylating the reaction product from step (c), the compound of formula (8), by treatment with an N-alkylating agent, such as formaldehyde, acetaldehyde or propanal, for example, in the presence of a reducing agent and under reaction conditions capable of reducing an iminium compound, and isolating the desired product of formula (1), in high chiral purity, A preferred embodiment of the alternate process for preparing compound (1), wherein Alk is methyl, is the process comprising:

(a) reacting the starting material, (S)-pyroglutamic acid, of formula (5),

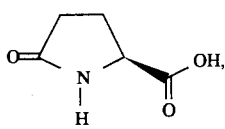
(5)

with methanol as the esterifying reagent at from −10° C. to 60° C. for from 4-to-48 hours, to prepare the (S)-pyroglutamic acid ester of formula (6),

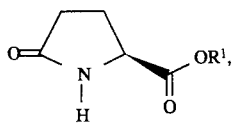
(6)

wherein $R^1$ is methyl;

(b) reacting the compound of formula (6) with an excess of a salt of the dianion of acetone oxime in a solution of THF:hexane, at a temperature of from −10° C. to ambient temperature, with vigorous mixing of the reagents, to form the intermediate product, 1-(1-methyl-5-oxo-2(S)-pyrrolidinyl)-1,3-butanedione-3-oxime, which is not isolated, but which is cyclized and dehydrated by reaction with a strong acid at ambient-to-reflux temperature for from 0.5- to - 3 hours, to produce the novel 5(S)-(3-methyl-5-isoxazolyl)-2-pyrrolidinone compound of formula (7),

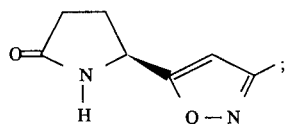
(7)

(c) reducing the compound of formula (7) with a reducing agent known to reduce lactams to cyclic amines, particularly an agent selected from the group consisting of lithium aluminum hydride, $NaBH_4/BF_3$, $NaBH_4/CH_3SO_3H$, $NaBH_4$/camphor sulfonic acid, borane/dimethyl sulfide, and borane/THF, to give the 3-methyl-5-(2(S)-pyrrolidinyl)isoxazole compound of formula (8),

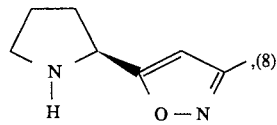
(8)

which is not isolated; then (d) immediately treating the reaction product from step (c) with the N-alkylating agent formaldehyde in the presence of formic acid at ambient or an elevated temperature, and isolating the desired product of formula (1), wherein Alk is methyl, in high chiral purity.

A more preferred embodiment of the alternate process is the process for preparing compound (1) wherein Alk is methyl, comprising:

(a) reacting the compound of formula (5) with methanol and sulfuric acid at about 60° C. for from 3.75-to-48 hours, to prepare the compound of formula (6), wherein $R^1$ is methyl;

(b) reacting the compound of formula (6) with 2.0 equivalents of the lithium salt of the dianion of acetone oxime in a solution of THF:hexane, wherein the ratio of THF:hexane is 3:2, and subsequently cyclizing and dehydrating with concentrated sulfuric acid as described above to produce the compound of formula (7);

(c) reducing the compound of formula (7) with borane in THF to produce the compound of formula (8), which is not isolated; and then (d) immediately N-methylating compound (8) with formaldehyde and formic acid at ambient temperature, and isolating the desired product, 3-methyl-5-(1-methyl-2-pyrrolidinyl)isoxazole, in high chiral purity.

Another alternate exemplification of the invention is the process for preparing compound (1) wherein Alk is methyl, comprising:

(a) reducing the CBZ-protected-L-proline of formula (9),

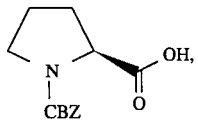
(9)

with a suitable reducing agent to give the CBZ-protected-L-prolinol of formula (10),

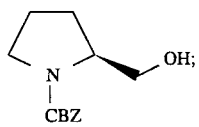
(10)

(b) selectively oxidizing the prolinol compound (10) to give the CBZ-protected-L-prolinal of formula (11),

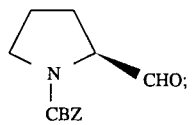
(11)

(c) condensing the compound (11) with an ylid derived from acetone to give the intermediate product of formula (12),

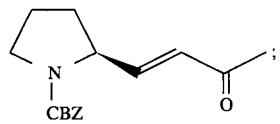
(12)

(d) converting the ketone compound (12) into its oxime by reaction with hydroxylamine in the presence of a weak organic base and a suitable solvent to give the compound (13),

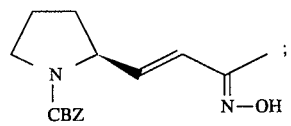
(13)

(e) cyclizing and dehydrating compound (13) by reaction with KI and $I_2$ in the presence of a weak organic base to give the protected intermediate compound (14),

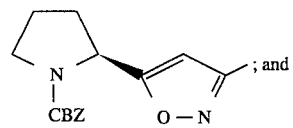
(14)

and (f) reductively cleaving the protecting group by reaction with a suitable hydride reducing agent and isolating the desired product, 3-methyl-5-(1-methyl-2-pyrrolidinyl)isoxazole, in high chiral purity.

It should be recognized that certain modifications to the alternate process will be obvious to those skilled in the art, and such changes are intended to be within the scope of this invention. For example, the order of steps (c) and (d) of the alternate process may be reversed without changing the intent of the invention.

It is intended that the process, in both original and alternate outline, will be carried out by skilled chemists who may make changes, such as preferably, but not necessarily, carrying out sequential reactions in the same vessel, or changing solvents or reaction temperatures or equipment, especially for economic reasons, and such modifications are to be considered within the scope of the present invention.

This process, in either form, may also be used to produce the enantiomerically-pure R-stereoisomer, beginning with the R-stereoisomer starting material.

This invention also discloses the novel compounds, 5(S)-(3-methyl-5-isoxazolyl)-2-pyrrolidinone (compound 7, above), 3-methyl-5-(1-methyl-2-pyrrolidinyl)-5-hydroxy-4,5-dihydro-isoxazole (compound 4, above) and 1-(1-methyl-2(S)-pyrroliclinyl)-1,3-butanedione-3-oxime (compound 3a, above), useful for the preparation of the compound of formula 1, above.

The term "$C_1$–$C_3$-alkyl, refers to an aklyl group of the side indicated, such as for example, methy, ethyl, or n-propyl,.

The term "cyclizing and dehydrating reagent" refers to a strong acid, as defined below, or a reagent, such as mesyl chloride, tosyl chloride or acetic anhydride, for example, for converting an hydroxy group to a derivative which acts as a leaving group under the conditions of the reaction, thereby initiating the cyclization reaction and catalyzing the dehydration of the ring thus formed.

The term "esterifying reagent" refers to esterification with methanol or ethanol, for example, in the presence of a strong acid, such as thionyl chloride, sulfuryl chloride, $H_2SO_4$, HCl, HBr, $BF_3$ or toluenesulfonic acid, with the optional presence of trimethyl orthoformate, triethyl orthoformate, 2,2-dimethoxypropane or 2,2-diethoxypropane, or with a reagent such as methyl iodide or ethyl iodide in the presence of a base, such as $K_2CO_3$ or diisopropylamine, under the conditions specified.

The term "N-alkylating agent" refers to a combination of reagents capable of alkylating an amine group, such as an aldehyde with a combination of a reducing agent and reaction conditions capable of reducing an iminium compound, or to an alkyl halide or dialkyl sulfate in the presence of a mild base, for example, a tertiary amine or an alkali metal carbonate; in particular, an "N-methylating reagent", as used herein, refers to a combination of reagents capable of methylating an amine group, such as the combinations of formaldehyde and formic acid; formaldehyde and sodium borohydride or sodium triacetoxyborohydride; formaldehyde or paraformaldehyde and hydrogen in the presence of a catalyst, such as Pd/C or Pd/BaSO$_4$; methyl iodide and triethylamine; or methyl iodide and an alkali metal carbonate or bicarbonate salt, under the conditions specified.

The term "strong acid" refers to those acids such as conc. $H_2SO_4$, HCl, p-toluenesulfonic acid, or a strongly acidic cationic ion exchange resin, such as Dowex® 50 or Amberlyte® IR-112, for example.

The following examples are provided as illustration and not limitation of the novel process of the invention.

The following abbreviations are used: DMF for dimethylformamide; e.e. for enantiomeric excess, which is a measure of enantiomeric purity; THF for tetrahydrofuran; TBME for t-butylmethyl ether.

EXAMPLE 1

Preparation Of 3-Methyl-5-(1-methyl-2(S)-pyrrolidinyl) isoxazole

1a. L-Proline methyl ester hydrochloride

To a solution of L-Proline (115 g,1 mol)in methanol (1.2 L) at 0° C. was added sulfuryl chloride (45 mL, 0.55 mol) slowly during ~15–20 min, then the reaction mixture stirred overnight at room temperature. After 16 hours at room temperature and another 4 hours at reflux, trimethyl orthoformate (120 mL, 1.1 mol) was added and heating at reflux continued for another 24 hr. The reaction mixture was then concentrated and the resultant oil was placed under high vacuum for several days to afford the product as a clear oil (205 g).

1b. N-Methyl proline methyl ester

A 10.42 g (62.92 mmol) sample of L-proline methyl ester hydrochloride(Aldrich Chemical Co.) was reductively methylated over 2.5 g of 10% Pd/C under 4 Atm of hydrogen in a solution containing 20 g of sodium acetate and 49.5 mL of 37% aqueous formaldehyde for 48 hours. Upon completion of the reaction, the methanolic solution was concentrated and the residue was dissolved in 10% aq. HCl (60 mL) and washed with ether (3×100 mL), then the aqueous layer was adjusted to pH ~12 with $K_2CO_3$ (solid) and extracted with methylene chloride (3×75 mL). The combined methylene chloride layers were dried (MgSO$_4$) and concentrated to afford the crude product as a clear oil (16.6 g, 77% yield).

1c.  1-(1-methyl-2(S)-pyrrolidinyl)-1,3-butanedione-3-oxime

To a solution of acetone oxime (Aldrich, 9.91 g, 135 mmol, 2.0 eq.; recrystallized 1x hexanes) in THF (100 mL) under argon at 0° C. was added n-BuLi (Aldrich, 1.6M in Hexane, 169 mL, 4.0 eq.) dropwise over a 20 minute period. After ~1.5 hours at 0° C. a solution of N-methyl proline methyl ester (9.71 g, 67.8 mmoL, 1.0 eq. the product of step 1b)in THF (10 mL) was added over a 15 minute period. After stirring an additional 5 hours at 0° C. the reaction mixture was slowly poured into a vigorously stirred solution of 10% aq. HCl (400 mL, cooled to 0° C. ), then the layers were separated and the aqueous layer was washed with ether (2×250 mL), then adjusted to pH ~9–10 with NaHCO$_3$/Na$_2$CO$_3$ (solid) and extracted with methylene chloride (4×150 mL). The combined methylene chloride layers were dried (MgSO$_4$) and concentrated to afford the crude product as a pale yellow oil (71%). MS (Cl, DCl/NH$_3$) m/e 185 (M+H)$^+$. $^1$NMR (CDCl$_3$) δ: 1.57–1.91 (br.m., 4H); 2.02 (s, 3H); 2.42–2.52 (m, 1H); 2.53 (s, 3H); 2.75 (dd, 1H); 2.80 (d, 2H); 3.15 (m, 1H).

1d. 3-Methyl-5-(1-methyl-2(S)-pyrrolidinyl)isoxazole

To a solution of the oxime product of step 1 c (8.88 g, 48.2 mmol, 1.0 eq.) in methylene chloride (200 mL) under argon at 0° C. was added triethylamine (8.73 mL, 62.6 mmoL, 1.3 eq.) followed by mesyl chloride (4.47 mL, 57.8 mmoL, 1.2 eq.) dropwise, then the reaction mixture was allowed to gradually warm to room temperature. After 20 hours the reaction mixture was quenched with 10% aq. HCl (150 mL), the methylene chloride was removed on a rotary evaporator, and the aqueous layer washed with ether (2×100 mL) then adjusted to pH ~9–10 with NaHCO$_3$/Na$_2$CO$_3$ (solid) and extracted with methylene chloride (4×100 mL). The combined methylene chloride layers were dried (MgSO$_4$) and concentrated to afford the crude product as a brownish oil (6.38 g). Chromatographic purification (silica; 5% methanolic CHCl$_3$) followed by vacuum distillation (b.p. ~80°–90° C. @2–3 mm Hg) afforded the product as a clear oil (2.62 g, 32%). $[α]_D^{23°}$= –13.1° (c 0.9, MeOH). MS (DCl/NH$_3$) m/e: 153 (M+H)$^+$. $^1$H NMR (CDCl$_3$) δ1.80– 2.00 (m, 3H), 1.99 (br s, 1H, NH), 2.14–2.21 (m, 1H), 2.28 (s, 3H), 2.96–3.16 (m 2H), 4.32 (dd, 1H), 5.95 (s, 1 H).

EXAMPLE 2

Intermediate-Scale Preparation of 3-Methyl-5-(1-methyl-2(S)-pyrrolidinyl)isoxazole hydrochloride 2a. 1- (1-methyl-2(S)-pyrrolidinyl)- 1,3-butanedione-3-oxime To n-BuLi (Aldrich, 2.5M in hexane, 61 4 mL, 1.53 mol, 4.4 eq.), diluted to 1.6M with hexane (342 mL), under argon at 0° C. was added a solution of acetone oxime (Aldrich, 56.15 g, 768 mmol, 2.2 eq.; recrystallized 1x hexanes)in THF (500 mL) dropwise over a 90 minute period (butane evolved! ). After an additional 2 hours at 0° C. a solution of N-methyl proline methyl ester (50.0 g, 349 mmoL, 1.0 eq., the product of step 1b above)in THF (75 mL) was added over a 90 minute period. After stirring an additional 20 hours at 0° C. the reaction mixture was slowly cannulated into a vigorously stirred solution of 10% aq. HCl (1700 mL, cooled to 0° C.) over a 40 minute period. The layers were separated and the aqueous layer was washed with ether (1000 mL), then adjusted to pH ~9–10 with $NaHCO_3$/$Na_2CO_3$ (solid) and extracted with methylene chloride (4×800 mL). The combined methylene chloride layers were dried ($MgSO_4$) and concentrated to afford the crude product as a pale yellow oil, (53.62 g), along with 10–20% of the N-oxide byproduct (by NMR integration). MS (Cl, DCl/$NH_3$) m/e 185 $(M+H)^+$. $^1$NMR ($CDCl_3$) δ: 1.57–1.91 (br.m., 4H); 2.02 (s, 3H); 2.42–2.52 (m, 1H); 2.53 (s, 3H); 2.75 (dd, 1H); 2.80 (d, 2H); 3.15 (m, 1H).

2b. 3-Methyl-5- (1-methyl-2(S)-pyrrolidinyl)isoxazole hydrochloride

To a solution of the oxime product of step 2a above (53.60 g, 291 mmol, 1.0 eq.) in $CH_2Cl_2$ (1000 mL) under argon at 0° C. was added triethylamine (52.71 mL, 378 mmoL, 1.3 eq.) followed by mesyl chloride (27.02 mL, 349 mmoL, 1.2 eq.) dropwise, then the reaction mixture allowed to warm to room temperature. After 18 hours the reaction mixture was extracted with 10% aq HCl (800 mL, 200 mL, 100 mL), the combined aqueous layers washed with $Et_2O$ (800 mL), then adjusted to pH ~9–10 with $NaHCO_3$/$Na_2CO_3$ (solid) and extracted with methylene chloride (4×500 mL). The combined methylene chloride layers were dried ($MgSO_4$) and concentrated to afford the crude product as a brownish oil. Vacuum distillation of this crude product afforded the amine, which was treated with ethereal HCl to afford the hydrochloride salt as a white solid (30.53 g, 43% yield from N-methyl proline methyl ester). Analytically pure product was obtained via recrystallization from EtOH/EtOAc. mp.= 155°–157° C. $[\alpha]_D^{23}$=−32.4° (c 0.58, MeOH). MS (DCl/$NH_3$) m/e 167 $(M+H)^+$, 184 $(M+NH_4)$. $^1$H NMR ($D_2O$, 300 MHz) δ 2.23–2.48 (m, 3H), 2.34 (s, 3H), 2.55–2.68 (m, 1H), 2.92 (br s, 3H), 3.33– 3.45 (m, 1H), 3.72–3.82 (m, 1H), 4.74–4.84 (partly buried in $H_2O$ peak, 1H), 6.65 (s, 1H). Anal. calcd. for $C_9H_{15}ClN_2O$: C, 53.33; H, 7.46; N, 13.82. Found: C, 53.52; H,7.49; N, 13.62.

EXAMPLE 3

Another Preparation of 3-Methyl-5-(1-methyl-2(S)-pyrrolidinyl)isoxazole

3a. N-Methyl (L)-proline

To 175 mL of methanol containing (L)-proline (33 g, 286.7 mmol) and 37 wt % of aqueous formaldehyde (24 mL) was added 10% Pd/C (1.65 g), and the reaction mixture was hydrogenated at 4 Atm of $H_2$. After the reaction was complete, the catalyst was removed by filtration, the filtrate was concentrated, and the residue was triturated with ether and dried under high vacuum. The crude product was obtained as a white powder (33.44 g, 90%). MS (DCl/$NH_3$) m/e 130 $(M+H)^+$, 147 $(M+NH_4)^+$; $^1$H-NMR ($D_2O$) d 1.94–2.23 (m, 4 H); 2.45–2.57 (m, 1 H); 2.94 (s, 3 H); 3.16 (m, 1 H); 3.74 (m, 1 H); 3.90 (dd, 1 H).

3b. N-Methyl (L)-Proline Methyl Ester

To a solution of N-methyl (L)-proline, from step 3a, in methanol at 0° C. is added thionyl chloride (1.1 eq) dropwise, and the reaction mixture is slowly allowed to warm to room temperature. Upon completion of the reaction the solvent is removed in vacuo, and the crude product is dissolved in 10% aq. HCl and washed with ether. The aqueous layer is adjusted to pH ~12 with $K_2CO_3$ (solid) and extracted with $CH_2Cl_2$. The combined $CH_2Cl_2$ layers are dried ($MgSO_4$) and concentrated to afford the crude product as a clear oil.

3c. 3-Methyl-5-(1-methyl-2(S)-pyrrolidinyl)isoxazole

The N-methyl (L)-proline methyl ester, from step 3b, is reacted according to the procedures of Example 1, steps c and d, to give the title product.

EXAMPLE 4

Another Intermediate Scale Preparation Of 3-Methyl-5-(1-methyl-2(S)-pyrrolidinyl)isoxazole 4a. (S)-Pyroglutamic acid methyl ester A 500 g sample of L-pyroglutamic acid was added to 2.8 L of anhydrous methanol, 28 mL of $H_2SO_4$ was added, and the mixture was stirred for 4 hr at 60° C. The reaction mixture was cooled to room temperature, 262 g of $NaHCO_3$ was added, and the mixture was stirred for an additional 16 hr. The mixture was dried by addition of 314 g of $Na_2SO_4$ with stirring for 1 hr, then the mixture was filtered and the solvent was evaporated under vacuum to yield a pale yellow oil. The oil was dissolved in THF, and a small amount of unreacted acid was filtered off. The THF was removed under vacuum, and the residual oil was dried by azeotropic distillation with toluene.

4b. 5(S)-($_3$-methyl-5-isoxazolyl)-2-pyrrolidinone

Acetone oxime (2.924 kg, 40 mol) was dissolved in 17.5 L of THF stirred under $N_2$, and the solution was cooled to −40° C. Addition of 8 L of n-butyllithium (10M in hexane, 6.19 kg) was carefully accomplished at a rate such that the temperature of the reaction did not rise above 5° C. To this solution was added 2.719 kg of the compound from step 4a above dissolved in 7 L of THF, also at a rate such that the temperature of the reaction did not rise above 5° C. After addition of the reactants, the mixture was stirred for 12 hr at room temperature. The mixture was cooled to 0° C., and 8.891 kg of $H_2SO_4$ and 4.8 L of water was added at a rate such that the temperature of the reaction did not rise above 35° C. The reaction was subsequently heated, and refluxing began at 60° C. The reaction was stirred for 1 hr, cooled to 20° C., and 9.32 kg of $Na_2CO_3$ was added slowly. The mixture, was filtered, then the filter cake was reintroduced into the reactor and stirred with 15 L of ethyl acetate for 1 hr. The solution was filtered, and the residue was washed with 2.5 L of ethyl acetate. The solutions were combined and evaporated to dryness. The residual dark oil was stripped with xylene to remove excess acetone oxime. The residue was dissolved in t-butylmethylether (TBME), and water was added. A tarry residue, which contained polar side-products, separated. The TBME solution was evaporated, and the residue was allowed to stand for 2 hr. A colorless oil containing apolar impurities rose to the top and was removed. The remaining residue was mixed with twice the volume of TBME and seeded, with subsequent crystallization occurring at room temperature. m.p=90°–91° C.

4c. 3-Methyl-5-(1-methyl-2(S)-Pyrrolidinyl)isoxazole

The compound from step 4b above (3.047 kg, 18.3 mol) was dissolved in 14 L of THF and placed under $N_2$. At room temperature, borane-TH F complex (55 L, 55 mol) was introduced at a rate such that the internal temperature remained at 30° C. At the end of the exothermic and foaming addition, the reaction was heated at reflux (67° C.) for 1 hr. The reaction mixture was then cooled to 0° C., and 8.2 L of methanol was slowly added so that the internal temperature remained at 20° C. The mixture was then stirred for 2 hr. at room temperature, and the solvent was evaporated under vacuum to yield a yellow oil, which solidified upon standing. This residue was emulsified with water and cooled to 10° C. A solution of formaldehyde (35%, 2.1 L, 27.5 mol) and formic acid (97%, 990 mL, 18.3 mol) was added to the emulsion, and the exothermic and effervescent reaction was maintained at an internal temperature below 30° C. The mixture was the cooled to 10° C., 1 kg (9.5 mol) of $Na_2CO_3$ was added in portions, and the mixture was stirred for 1 hr. NaOH (10%, 2.29 L) was added, followed by 5.5 L of water. The product was isolated by extraction with ethyl acetate, which was dried over $MgSO_4$, filtered and concentrated to dryness. The product was double distilled, dissolved in ethyl acetate, converted to the HCl salt with ethanolic HCl, recrystallized from ethyl acetate, suspended in ethyl acetate, re-converted to the base with treatment with 30% NaOH solution, the layers separated, the organic layer washed with brine, dried and evaporated, to yield the product, which was finally distilled to yield 490 g of the pure title product (e.e. =99.5%).

EXAMPLE 5

Large Scale Preparation of 3-Methyl-5-(1-methyl-2(S)-pyrrolidinyl)isoxazole 5a. (S)-Pyroglutamic acid methyl ester Methanol (62 L, 1.155 mol), L-pyroglutamic acid (20 kg, 154.9 mol) and $H_2SO_4$ (97%, 0.87 L, 15.5 mol) were introduced into a reactor. The suspension was warmed to 60° C. and stirred until the pyroglutamic acid concentration dropped below 10%. The temperature of the reactor jacket was lowered to 0° C., and when the internal temperature reached 30° C., 9.7 kg (68.1 mol) of $Na_2SO_4$ was added and stirred for 15 min, then 8.1 kg (96.4 mol) of $NaHCO_3$ was added. When pH 7 was reached (about 10 min), the suspension was filtered over a pad of celite. The filtrate was reintroduced into the reactor, and the methanol was distilled off at a pressure of 90–160 mbar and a jacket temperature of 50° C. Ethyl acetate (53 L) was then added with stirring, the mixture cooled to 0° C., and the mixture stirred for 16 hr. Unreacted pyroglutamic acid crystallized out and was removed by filtration. Removal of the ethyl acetate by evaporation under reduced pressure provided the title product as a viscous yellow oil, which was taken to the next step without further purification.

5b. (S)-N-methyl-pyroglutamic acid methyl ester

The methyl ester compound from step 5a above (18.3 kg, 127.8 mol) and dimethyl sulfate (20.09 kg, 159.3 mol) were introduced into a reactor, and the mixture was heated to 60° C. under an $N_2$ atmosphere. Heating was continued until the concentration of starting material dropped below 15%. An additional 6.25 kg (0.5 eq) of dimethyl sulfate was added with exothermic response. The thick reaction mixture was then cooled to 25° C., and a solution of triethylamine (16.12 kg) in diethyl ether (19.2 L) was added at such a rate that the temperature did not rise above 30° C. The emulsion was washed with two 50 L portions of water. The ether layer was separated, and the residue was extracted with ethyl acetate (60 l). The combined organic layers were dried over $Na_2SO_4$ and azeotroped with toluene until no more triethylamine remained in the residue. The residue was mixed with dimethyl sulfate (1.7 kg, 13.5 mol) and THF (70 L) and refluxed under nitrogen until the reaction was complete. The solvents were evaporated under vacuum, and the residue was distilled under high vacuum to yield a colorless product.

5c. 3-Methyl-5-(1-methyl-2(S)-pyrrolidinyl)isoxazole

THF (56.7 L) was placed in a cryogenic reactor, and acetone oxime (4.4 kg, 73.1 mol) was added under nitrogen, and the solution was cooled to –40° C. Under nitrogen, n-butyllithium (10M in hexane, 13 L, 64.06 mol) was added at a rate such that the internal temperature did not exceed 5° C. (extremely exothermic reaction), and then stirred for 2 hr at 0° C. To this solution was added the compound from step 5b above, at a rate such that the internal temperature did not exceed 5° C. At the end of the addition, cooling was discontinued, and the mixture was stirred for 16 hr at room temperature. The thick suspension was cooled to 0° C. and treated with a mixture of $H_2SO_4$ (12.52 kg, 123 mol) and ice water (7 kg) with vigorous stirring while maintaining the internal temperature at less than 10° C. The mixture was next heated to reflux temperature and held at that temperature four 1 hr (butane was evolved). The mixture was then cooled to room temperature, and 21.08 kg (152.5 mol) of $K_2CO_3$ was added in portions, with stirring until pH>7 was reached, then filtered. The filter cake was washed with ethyl acetate (26.6 L), and the filtrate was evaporated under vacuum and azeotroped three times with xylene (10 L). The residue was dissolved in ethyl acetate (14 L) and washed with 1M HCl (7 L). The aqueous phase was back extracted with ethyl acetate (3×14 L). The combined organic phases were dried over $MgSO_4$ and filtered over silica gel. The filter cake was washed with 5 L of ethyl acetate. The combined organic layers were evaporated to dryness in a rotary evaporator, and the resulting oil was taken directly to the next step without further purification. The oil (3.17 kg, 18.3 mol) was dissolved in 13.8 L of THF and stirred under nitrogen. Borane-THF complex (1M, 55 L, 55 mol) was introduced at a rate such that the internal temperature did not rise above 30° C. The mixture was stirred for 30 min, then cooled to 0° C., 11.1 L of HCl (1M, 55 mol) was added, then refluxed for 30 min. The THF was distilled off under reduced pressure, and the resulting suspension was filtered. The residue was washed with water. The combined filtrates were neutralized with said $K_2CO_3$ solution and extracted with 30 L of diethyl ether. The organic phase was dried over $MgSO_4$ and concentrated under vacuum. The residue was redissolved in ethyl acetate, and washed once with 2M HCl and twice with 1M HCl. The combined aqueous solutions were extracted twice with ethyl acetate and stirred with ethyl acetate, ice and 30% NaOH. The ethyl acetate extracts were combined, washed with brine, then dried over $MgSO_4$ and stirred with 0.3 kg of silica gel for 10 min. The mixture was filtered and the solvents were evaporated to dryness in a rotary evaporator to yield 2.58 kg of an oil. The oil was dissolved in ethyl acetate and cooled to 0° C., then 1.88 kg (15.5 mol, 1 eq) of an 30.1% ethanolic HCl solution was added. The solution was seeded and stirred for 2 hr. Crystals were filtered off, washed with ethyl acetate, and dried under high vacuum. The mother liquor was diluted with 10 L of ethyl acetate and stirred with 2.3 L of 30% NaOH. The phases were separated, and the aqueous phase was extracted with ethyl acetate. The combined organic layers were washed with brine and dried over MgSO$_4$, then concentrated to recover the base for a second crop. The crystalline hydrochloride salt (1.68 kg) was suspended in 4 L of ethyl acetate, which was then vigorously mixed with 4 L of 1N NaOH. The phases were separated, and the aqueous phase was extracted with ethyl acetate. The combined organic layers were washed with brine and dried over MgSO$_4$, then evaporated under vacuum. The product was distilled at 92° C. at 12–13 mm Hg (e.e.=99.5%).

EXAMPLE 6

Another Large Scale Preparation of 3-Methyl-5-(1-methyl-2(S)-pyrrolidinyl)isoxazole 6a. N-Methyl-proline methyl ester Methanol (2.:2 L, 68.66 mol) was stirred under nitrogen and cooled to 0° C. Sulfuric acid (97%, 0.179 L, 3.26 mol) was added with vigorous stirring at a rate such that the internal temperature of the reactor did not rise above 10° C. L-Proline (0.5 kg, 4..34 mol) was added to the methanol, and the reaction was refluxed for 18 hr. The reaction mixture was cooled to 0° C., and with vigorous stirring a solution of K$_2$CO$_3$ (0.217 kg, 1.57 mol) in 0.363 L of water was slowly added to the mixture, until the pH was between pH 7 and 8. The neutralized solution was again cooled to 0° C., and aqueous formaldehyde solution (36%, 0.543 L) was added. After stirring for 15 min, 0.082 kg (2.17 mol) of powdered sodium borohydride was added in portions while maintaining the temperature between –5° and +5° C. The suspension was stirred for 3 hr, then filtered, and the filter cake was washed with toluene. The combined organic solvents were diluted 1:1 with water (2.6 l) and filtered. The organic phase was separated, and the aqueous layer was extracted at 0° C. with 5×0.5 L portions of toluene. The toluene extracts were combined, dried over sodium sulfate and filtered. The volume of the solution was reduced by half by distillation at 60° C. and 90 mbar pressure. The solution was taken to the next step without further purification.

6b. 3-Methyl-5-(1-methyl-2(S)-pyrrolidinyl)isoxazole

THF (36.4 L) was stirred under nitrogen, and acetone oxime (3.034 kg, 41.5 mol) was added. The solution was cooled to –40° C., and n-butyllithium (10M in hexane, 8.3 L, 83 mol) was added at a rate such that the internal temperature did not rise above 5° C. (very exothermic reaction). Stirring was continued for an additional 2 hr, with the temperature maintained between 0° and 5° C. Under nitrogen THF (16.6 L) was added and the mixture was cooled to –10° C. The solution of N-methyl proline methyl ester, from step 6a above, was diluted with 3.3 L of THF (to a total of 23.5 L) and cooled to 0° C. Into a third reactor containing a small amount to THF, the solutions of the acetone oxime dianion and the ester were simultaneously added dropwise at the ratio of dianion to ester of 2:1. The internal temperature of the reaction vessel was maintained between –12° and –6° C., and the temperatures of the added solutions were 5° C. After addition was complete, the reaction mixture was stirred for 1 hr at –10° C. To the reaction was added a mixture of 97% sulfuric acid (10.99 kg, 108.7 mol) in ice water (6.177 kg) in portions such that the temperature did not rise above 10° C. The solution was heated at reflux for 3 hr with vigorous stirring, and 25 L of THF was distilled off. The mixture was cooled to 25° C., and solid Na$_2$CO$_3$ (7.687 kg, 72.5 mol) was added in portions, with vigorous stirring. The yellow precipitate was filtered and washed with 2×12.5 L portions of THF. The filtrate was evaporated in a rotary evaporator and azeotroped with 3×3 L of toluene. The residue was filtered through a column of silica gel, and the product was eluted with 41.5 L of 3% methanol in ethyl acetate. The eluate was evaporated to dryness, and the product was vacuum distilled (0.1 mbar, 70° C., e.e.=99.5%).

EXAMPLE 7

Another Preparation of N-Methyl-L-proline Methyl Ester

The procedure of Example 13a is repeated, replacing the aqueous formaldehyde solution with methanolic paraformaldehyde solution, and hydrogenating in the presence of 10% Pd/C under 4 Atm of H$_2$ at 50° C. The catalyst is filtered off, and the solvent and unreacted aldehyde are removed by evaporation under vacuum. The residual N-methyl-L-proline is then dissolved in and reacted with methanol in the presence of H$_2$SO$_4$ at reflux for 4–24 hr. The reaction mixture is cooled to 0° C., and with vigorous stirring a solution of K$_2$CO$_3$ is slowly added to the mixture, until the pH is between pH 7 and 8, then the title product is extracted from the basic mixture and isolated after drying and removal of the solvent.

EXAMPLE 8

Another Preparation of N-Methyl-L-proline Methyl Ester

The L-proline is dissolved in methanol, the solution is cooled to 0° C. and 36% aqueous formaldehyde is added with stirring. To this solution is then added powdered NaBH$_4$ in portions while maintaining the temperature between –5° and +5° C. The reaction is filtered, the filter cake extracted with solvent and combined with the filtrate, and the solvents evaporated to dryness. The residual N-methyl-L-proline is then dissolved in and reacted with methanol in the presence of H$_2$SO$_4$ at reflux for 4–24 hr. The reaction mixture is cooled to 0° C., and with vigorous stirring a solution of K$_2$CO$_3$ is slowly added to the mixture, until the pH is between pH 7 and 8, then the title product is extracted from the basic mixture and isolated after drying and removal of the solvent.

Another Preparation of 3-Methyl-5-(1-methyl-2(S)-pyrrolidinyl)isoxazole

9a. Preparation of the Na/Li salt of the dianion of acetone oxime

Acetone is dissolved in methanol and reacted with 1.1 equivalents of hydroxylamine dihydrogen sulfate salt at 60° C. To this solution is then added 2.2 equivalent of sodium methoxide, and the reaction is heated at reflux until complete. The solvents are removed by evaporation under vacuum, and the residue is dried under vacuum. The residue is dissolved in anhydrous THF, cooled to –10° C., then 1.3 equivalents of n-butyllithium are added at a rate such that the temperature; is maintained between –10° and 0° C.

9b. 3-Methyl-5-(1-methyl-2(S)-pyrrolidinyl)isoxazole

The solution of the Na/Li salt of the dianion of acetone oxime from step 9a above is then substituted for the dilithium salt of the dianion in Example 6 and the reaction is conducted according to the procedure of Example 6 to prepare and isolate the title compound.

EXAMPLE 10

Acetonitrile Route to Preparation of 3-Methyl-5-(1-methyl-2(S)-pyrrolidinyl)isoxazole 10a N-Methyl-proline methyl ester A 2-L three neck round-bottom flask equipped with an overhead stirrer, internal temperature monitor, and addition funnel was charged with N-methyl proline (155.3 g, 1.20 mole) and methanol (800 mL). The vessel was chilled to 0° C. and sulfuryl chloride (110 mL, 1.33 mole) was added dropwise via the addition funnel at a rate such that the internal temperature remained ≦+15° C. The cold bath was replaced with a heating mantle and trimethyl orthoformate (150 mL, 1.37 mole) was added quickly over 5 min. The reaction was heated to gentle reflux for 5 hours, then cooled to room temperature. The bulk of the solvent was evaporated in vacuo. The remainder was basified with saturated $Na_2CO_3$ solution (ca. 1 L, pH 9–10) and partitioned with ethyl acetate (1 L). The aqueous phase was extracted with ethyl acetate (4×500 mL), and the combined organics were washed with brine (1×1 L) and then dried ($Na_2SO_4$). After filtration and solvent evaporation the residue was distilled at reduced pressure (13 mm Hg, bp 56° C.) to give 125.7 g (73% yield, ≧99% ee).

10b. (S)-(N-methyl-2-pyrrolidinyl)cyanomethyl ketone

A 3-L three neck round-bottom flask equipped with an overhead stirrer, addition funnel, internal temperature monitor, and $N_2$ inlet was charged with sodium amide (97.9 g, 2.25 mole) and tetrahydrofuran (1350 mL). The suspension was cooled to ca. –40° to –45° C. and a solution of acetonitrile (135 mL, 2.58 mole) and tetrahydrofuran (75 mL) was added dropwise at such a rate that the internal temperature remained ≦–36° C. The nearly homogeneous solution was stirred ca. 13 min and was then added via a dry ice cooled cannula to a 5-L three neck round-bottom flask equipped with an overhead stirrer, internal temperature monitor and nitrogen outlet and charged with a solution of N-methylproline methyl ester (125.5 g, 0.876 mole) and tetrahydrofuran (1350 mL) cooled to ca. –40° to –45° C. The internal temperature was maintained ≦–40° C. throughout the addition. After 1 hr the reaction was quenched by the addition of solid ammonium chloride. (131 g, 2.45 mole). The cold bath was removed and the reaction was allowed to warm to +5° C. over about 1.5 h. Filter-aid (250 g) was added, and the mixture was filtered through a pad of filter-aid (250 g, 2" h ×6" diam.) topped with sand (500 g). The filter cake was washed with THF (ca. 1 L) to remove most of the color. The filtrate was concentrated in vacuo and the foamy orange residue, 267.2 g, was used directly in the next step.

10c. (s)-3-Oxo-1-methyl-3-(N-methyl-2-pyrrolidinyl)-1-propenamine

A 3-L three neck round-bottom flask equipped with an overhead stirrer, addition funnel, internal temperature monitor, and $N_2$ inlet was charged with the above crude ketonitrile (267 g, ca.0.87 mole) dissolved in tetrahydrofuran (1 L) and chilled to –5° to –10° C. Methyl magnesium chloride (930 mL, 3M THF, 2.79 mole) was added via addition funnel at such a rate as to maintain the internal temperature ≦+5° C. Following the addition the cold bath was removed, and the reaction was allowed to warm to room temperature and stir 15 hr. The dark mixture was carefully poured into ice (1.5 kg) and stirred 5–10 min. The aqueous portion was exhaustively extracted with ethyl acetate (ca. 15 to 20×1 L). The combined organics were dried ($Na_2SO_4$), filtered, and evaporated leaving 158.2 g dark oil used directly in the next step.

10d. (S)-3-methyl-,5-(N-methyl-2-pyrrolidinyl)isoxazole

A 2-L three neck round-bottom flask equipped with an overhead stirrer, reflux condenser, internal temperature monitor, and $N_2$ inlet was charged with the above crude ketoenamine (158 g, ca. 0.87 mole), acetonitrile (1000 mL), and hydroxylamine hydrochloride (64.0 g, 0.92 mole) and stirred at room temperature for 6 hours. Aqueous 50% sulfuric acid (9.4M, 240 mL, 2.26 mole) was added, and the mixture was heated to reflux for 1 hr. After cooling, the bulk of the solvents were removed in vacuo. The residue was basified by the addition of saturated sodium carbonate solution (ca 1.2 L, to pH 9–10), saturated with sodium chloride, and extracted with ethyl acetate (4×500 mL). The combined organics were washed with brine (1×1 L) and then dried ($MgSO_{4+}$ activated carbon). The mixture was filtered, the filtrate was concentrated and the residue was distilled at reduced pressure (10 mm Hg, bp 98°–101° C.) to give 71.97 g light yellow oil (49% overall yield from ester, ≧98% ee). Analytical data agree with that of Example 1, above.

EXAMPLE 11

Large Scale Preparation via Acetonitrile Route to 3-Methyl-5-(1-methyl-2(S)-pyrrolidinyl)isoxazole hydrochloride 11a. (S)-1-Methyl-2-pyrrolidinecarboxylic acid methyl ester L-Proline (46 kg), paraformaldehyde (13.2 kg), palladium on carbon (5%, 350 g) and methanol (158 kg) were charged into a hydrogenation reactor and hydrogenated at 40 psi for 6 hr. The mixture was filtered, and the filtrate returned to a reaction vessel. Trimethyl orthoformate (170 kg) and thionyl chloride (171 kg) were added, and the mixture was heated at reflux for 2 hr. The volatiles were then removed by distillation under vacuum. The residue was dissolved in methylene chloride (215 kg), and aqueous sodium carbonate solution (10%, 360 kg) was added to the mixture. After vigorous mixing, the methylene chloride layer was separated. The aqueous layer was extracted with methylene chloride (215 kg), and the extract combined with the first organic extract. The solvent was dried with sodium sulfate (anhydrous, 40 kg) and filtered. The volatiles were removed by distillation under vacuum, and the residue was distilled under high vacuum (10 mm Hg) to yield the product (34.5 kg, 60% yield).

11b. 3-Methyl-5-(1-methyl-2(S)-pyrrolidinyl)isoxazole hydrochloride

A solution of 31.4 kg of the ester compound from step 11a above, and acetonitrile (18 kg) dissolved in THF (19 kg) was added to a suspension of sodium amide (20 kg) in THF (195 kg) at –15° C. and stirred for 2 hr. Ammonium chloride (25.9 kg), methanol (10 kg) and THF (50 kg) were charged into the reactor. The mixture was stirred, then filtered, and the volatiles were distilled off under vacuum. The residue was dissolved in THF (170 kg), and methyl magnesium chloride (3M, 189 kg) was added to the mixture. The reaction was stirred for 8 hr, then quenched with water (44 kg) and aqueous sulfuric acid solution (25%, 114 kg). The volatiles were again removed under vacuum, and the pH of the residue adjusted to approximately pH 7 with aqueous sulfuric acid solution. To the residue was added 16.8 kg of hydroxylamine, and the mixture was stirred for 3 hr. The reactor was then charged with 15 kg of conc. sulfuric acid, and the mixture was heated at 70° C. for 3 hr. The mixture was cooled, and aqueous sodium hydroxide (50%) was added to adjust to approximately pH 11. The product was then co-distilled out of the mixture with water. Sodium chloride was added to the distillate, which was then extracted with ethyl acetate. The organic extract was dried over sodium sulfate, filtered, and concentrated to yield the crude product as an oil. The oil was distilled under high vacuum to yield 14 kg of a colorless oil, which was then dissolved in ethyl acetate. The ethyl acetate solution was charged into a solution of HCl gas in ethyl acetate. The resulting salt was filtered, then dried at 45° C. under vacuum to give 15.4 kg of the title product. The salt was recrystallized from acetone, filtered and dried at 50° C. under vacuum to give 11.6 g of the pure title compound

EXAMPLE 12

Preparation of 3-Methyl-5-(1-methyl-2(S)-pyrrolidinyl) isoxazole Via N-(1-methylethylidine)cyclohexanamine 12a. 3-(Cyclohexylamino)-1-(1-methyl-5-pyrrolidinyl)-2-butene-1-one Diisopropylamine (2.12 g, 21 mmol) and THF (35 mL) were added to a three-necked flask, which was flushed with $N_2$. The solution was stirred with ice cooling, and n-butyllithium (1.6M in hexane, 12.5 mL, 20 mmol) was added dropwise over 20 min. To the resulting solution was added N-(1-methylethylidine)cyclohexanamine (prepared via the procedure of *J. Org. Chem.*, 19:1054, 1954), over a 15 min period while maintaining the temperature at 0°±2° C., and the resulting solution was stirred at 0° C. for 20 min. To this solution was added 1.43 g (10.0 mmol) of N-methyl proline methyl ester over a 1 hr period, with stirring and cooling to maintain a temperature of 0°±2° C. The reaction was quenched by rapid addition of saturated aqueous ammonium chloride solution (10 mL). The layers were separated, and the aqueous layer was extracted one with 10 mL of ethyl acetate. The organic layers were combined and dried over $Na_2SO_4$. The solution was decanted from the solids and concentrated on a rotary evaporator to provide the product as a viscous oil (2.50 g). $^1H$ NMR (CDCl$_3$),δ:11.18 (br, 1H), 5.20 (s, 1H),3.40 (m, 1H), 2.62 (m, 1H), 2.33 (s, 3H), 2.21 (m, 1H), 1.97 (s, 3H), 1.9–1.5 (m, 8H), 1.5–1.0 (m, 6H), $^{13}C$ NMR (CDCl$_3$),δ:197.48 (s), 163.21 (s), 91.07 (d), 74.43 (d), 56.93 (t), 51.50 (d), 41.34 (q), 36.33 (t), 33.61 (t), 33.58 (t), 30.91 (t), 25.22 (t), 24.26 (t), 23.07 (t), 18.71 (q).

12b. 3-Methyl-5-(1-methyl-2(S)-pyrrolidinyl)isoxazole

Hydroxylamine HCl (70 mg, 1.0 mmol) was added to a solution of 3-(cyclohexylamino)-1-(1-methyl-5-pyrrolidinyl)-2-butene-1-one (160 mg, 0.64 mmol, from step 12a above) in 5 mL of methanol, and the mixture was stirred at 20°±5° C. for 4 hr. The solvent was removed under vacuum at 25° C., and the residue suspended in 3 mL of water and 1 mL of $H_2SO_4$. The mixture was heated to 70° C. for 90 min, then cooled to room temperature and adjusted to pH 10 with 50% NaOH (4 g). The mixture was extracted with ethyl acetate, and the extracts were dried over $Na_2SO_4$ and concentrated. The residue was confirmed as title product by chromatographic analysis. The analytical data correspond to that given in Example 1.

EXAMPLE 13

3-Methyl-5-(1-methyl-2(S)-pyrrolidinyl)isoxazole 13a. (S)-Pyroglutamic methyl ester To methanol (30.0 mL), cooled to −10 to −15° C., was slowly added sulfuryl chloride (11.0 mL, 178 mmol), DMF (0.133 mL) and L-pyroglutamic acid (L=(S) configuration, 10.0 g, 77.5 mmol, Sigma Chemical Co.). The stirred mixture was allowed to warm slowly and then stirred at room temperature for 36 hours. The methanol was removed under vacuum, and the residue was dissolved in ethyl acetate (400 mL). Water (~10 mL) was added, followed by the addition of sodium carbonate until basic. The organic layer was decanted, the slurry was washed with ethyl acetate (4×15 mL), and the organics were then combined and dried over magnesium sulfate. Removal of the solvent gave crude pyroglutamic methyl ester (10.04 g, 91%). NMR and MS analysis indicated >95% purity.

13b. 5(S)-(3-methyl-5-isoxazolyl)-2-pyrrolidinone

To a cooled (0°–5° C.) solution of acetone oxime (11.74 g, 160.8 mmol)in THF (200 mL) was slowly added n-butyl lithium (128.6 mL, 2.5M, 321.6 mmol)in hexanes. After being stirred at 0°–5° C. for one hour, a solution of pyroglutamic methyl ester (10.0 g, ~69.9 mmol, the product of step 13a)in THF (50 mL) was added. After stirring for 4 hr, the solution was allowed to slowly warm up to room temperature, and the stirring was continued for 16 hr. Sulfuric acid (35 g, 98%) was slowly added with cooling, followed by the addition of water (35 mL). The resulting mixture was refluxed for one hour. The organic layer was decanted and the slurry was washed with ethyl acetate (5×50 mL). To the mixture was added ethyl acetate (400 mL) and sodium carbonate until basic. Again, the organic layer was decanted and the slurry was washed with ethyl acetate (4×20 mL). The combined organics were then dried over magnesium sulfate. Evaporation of the solvents gave the title product (5.33 g, 46%), which was taken directly to the next step. HPLC (analytical Chiralark AD column) analysis indicated >99.6% ee.

13c. 3-Methyl-5-(1-methyl-2(S)-pyrrolidinyl)isoxazole

To a solution of crude 5(S)-(3-methyl-5-isoxazolyl)-2-pyrrolidinone (5.33 g, 32.1 mmol, the product of step 13b) in THF (50 mL) was added borane-THF (99.5 mL, 1.0M, 99.5 mmol) slowly at room temperature. The reaction mixture was heated at reflux for two hours. After removal of THF under vacuum, a solution of formaldehyde (10.0 mL) and formic acid (5.0 mL) was carefully added, and the reaction mixture was refluxed for one hour. Ethyl acetate (300 mL) was added, followed by the addition of sodium carbonate until basic. The organic layer was decanted, and the residue was washed with ethyl acetate (4×20 mL). The combined organic solvents were dried over sodium carbonate. The solvent was evaporated, and the, residue was distilled (bp. ~150° C./~50 mm Hg) to give the title compound (3.12) g, 59%; 24% overall yield). The compound was further purified by HPLC chromatography (CHCl$_3$/MeOH, 20:1 and 10:1). HPLC (analytical Chiralark OD column) analysis indicated >99% ee. [α]$_D^s$=−13.1 ° (c 0.9, MeOH). MS (DCl/NH$_3$) m/e: 153 (M+H)$^+$. $^1H$ NMR (CDCl$_3$) δ1.80–2.00 (m, 3H), 1.99 (br s, 1H, NH), 2.14–2.21 (m, 1H), 2.28 (s, 3H), 2.96–3.16 (m, 2H), 4.32 (dd, 1H), 5.95 (s, 1H).

EXAMPLE 14

Intermediate Scale Preparation of 3-Methyl-5-(1-methyl-2(S)-pyrrolidinyl)isoxazole 14a. (S)-Pyroglutamic acid methyl ester Sulfuryl chloride (388 mL, 5.31 mol) was added dropwise to methanol (930 mL), protected from moisture and cooled in an ice bath to keep the temperature under 15° C. When the addition was complete and the temperature had fallen to 4° C., (S)-pyroglutamic acid (301 g, 2.33 mol, Sigma Chemical Co.) was added in one portion. The ice bath was allowed to melt and the reaction mixture was stirred at ambient temperature for 16 hours. The solvent was removed on a rotary evaporator leaving 471 g of the crude product as a thick oil. Ethyl acetate (4 L), sodium carbonate (100 g), and 2M aqueous sodium carbonate (150 mL) were added, and the mixture was stirred vigorously for 1 hour. The organic layer was decanted from the semi-solid inorganic residue, and the residue was extracted with ethyl acetate. The organic fractions were combined and reduced on the rotary evaporator to give 343 g of thick yellow oil. The crude ester was vacuum distilled at 143°–145° C. and 0.35 torr to afford the title product (309.6 g, 92.8 % yield) as a colorless oil.

14b. 5(S)-(3-methyl-5-isoxazolyl)-2-pyrrolidinone

A 12-L Morton flask was equipped with an addition funnel, overhead stirrer, nitrogen inlet, thermoprobe, and surrounded with an ice water bath. The flask was charged with a solution of acetone oxime (146.2 g, 2.00 mol) in tetrahydrofuran (1.75 L), and n-butyllithium (2.5M in hexanes, 1.60 L, 4.00 mol) was added dropwise keeping the internal temperature under 10° C. After addition was complete, a solution of (S)-pyroglutamic acid methyl ester (133.1 g, 0.93 mol, the product of step 14a) in tetrahydrofuran (700 mL) was added dropwise, keeping the temperature under 10° C. The ice bath was allowed to melt, and the resulting mixture was stirred for 16 hr. The reaction was cooled in an ice bath while concentrated sulfuric acid (234 mL, 4.40 mol) was added dropwise, very slowly at first, followed by water (230 mL). The two-phase mixture was heated at reflux for 90 min, then cooled to room temperature, and the red THF/hexane organic layer was decanted from the semisolid aqueous inorganic residue. The residue was extracted with ethyl acetate (3×500 mL), then solid sodium carbonate (ca. 200 g) was added to the residue until basic, and it was again extracted with ethyl acetate (3×500 g). The decantate and the ethyl acetate extracts were combined, dried (MgSO$_4$), filtered, and the volatiles removed on the rotary evaporator to give a thick red oil (ca. 140 g).

The crude product was purified by column chromatography on silica gel, eluting with chloroform/methanol, 92/8 to give 87.6 g of the title compound as a pink crystalline mass. This was further purified by slurrying and washing with diethyl ether to give off-white fluffy crystals, 60.2 g (39 % yield), mp 90°–91° C. MS (DCl/NH$_3$) M/Z: 167 (M+H)$^+$, 184 (M+NH$_4$)$^+$. $^1$NMR (CDCl$_3$) δ:2.30 (s, 3H), 2.18– 2.65 (m, 6H), 4.88 (dd, 1H, J=8.1, J=4.5 Hz), 6.05 (s, 1H), 4.88 (s, 3H). [α]$_D$=9.47° (23° C., c=0.94, MeOH).

14c. 3-Methyl-5-(1-methyl-2(S)-pyrrolidinyl)isoxazole

A solution of 5(S)-(3-methyl-5-isoxazolyl)-2-pyrrolidinone (74.0 g, 0.44 mol, the product of step 14b) was prepared in a 5 L Morton flask fitted with an addition funnel, overhead stirrer, and nitrogen inlet. A solution of borane in tetrahydrofuran (1.0M, 1.33 L) was added at a moderate rate (ca. 20 min). The reaction was heated to reflux for 90 min, cooled to ambient temperature, and methanol (200 mL) added to quench the excess borane. The volatiles were removed on a rotary evaporator, and the residue co-stripped with methanol (3×100 mL) to leave 74 g of a thick, almost colorless oil.

A solution of 37 % aqueous formaldehyde (75 mL) was added dropwise to the thick oil, followed by the addition of formic acid (75 mL), and the mixture was heated on the steam bath for 30 min. The pale yellow solution was cooled in a water bath and sodium carbonate (50 g) was added portionwise with stirring, followed by the addition of 10 % sodium hydroxide solution (ca. 150 mL) until the pH=12. The resulting mixture was extracted with ethyl ether (6×150 mL), the extracts combined, dried (MgSO$_4$), filtered, and the volatiles removed on the rotary evaporator to leave the crude product as a yellow oil, 74 g. Distillation gave 61.9 g (83.6 % yield) of the purified title compound as a colorless mobile liquid, bp 92° C. at 13 torr. The analytical data agreed with that of Example 1 above.

EXAMPLES 15–22

Preparations of 3-Methyl-5-(1-methyl-2(S)-pyrrolidinyl)isoxazole With Various Molar Equivalents of Dianion The procedures of Example 13 were followed, except that the quantity of starting material, (S)-pyroglutamic acid was varied as shown in Table 1 below, and the molar equivalents of the acetone oxime dianion of step 13b were varied, also as shown in Table 1 below, with the yield of the title product in each experiment also shown.

TABLE 1

| Yield of product based upon amounts of starting material and acetone dianion | | | |
|---|---|---|---|
| Example number | Starting material (mmol) | Ratio of dianion to starting material* | % Yield |
| 15 | 2 | 1.1 | <30 |
| 16 | 2 | 1.3 | <40 |
| 17 | 2 | 1.5 | <40 |
| 18 | 2 | 1.7 | 62 |
| 19 | 3.5 | 1.8 | 81 |
| 20 | 3.5 | 1.9 | 70 |
| 21 | 354 | 2.0 | 45 |
| 22 | 30 | 2.3 | 80 |

*Equivalents of dianion acetone oxime per mmol of starting material

EXAMPLE 23

Preparation of 3-Methyl-5-(1-methyl-2(S)-pyrrolidinyl) isoxazole From CBZ-protected L-proline 23a. CBZ-L-prolinol To Carbobenzyloxy-L-proline (Aldrich, 9.80 g, 39.3 mmol)in THF (100 mL) at 0° C. was added BH$_3$-THF complex (Aldrich, 1M in THF, 100 mL, 100 mmol). The mixture was stirred at 0° C. for 2 hours, then at ambient temperature for 16 hr. The reaction mixture was poured into pH 7 phosphate buffer solution (500 mL) and ether (600 mL) and mixed well. The layers were separated and the aqueous portion was extracted with ether (500 mL). The combined organic layers were washed with brine (500 mL),dried (Na$_2$SO$_4$) and filtered. The solvents were evaporated in vacuo leaving the crude carbobenzyloxy-L-prolinol as an oil (10.5 g).

23b. CBZ-L-prolinal

Following the method of Leanna et al. (M. Robert Leanna, Thomas J. Sowin, Howard E. Morton, *Tetrahedron Lett.*, 1992, 33(35), 5029–5032), carbobenzyloxy-L-prolinol (9.23 g, 39 mmole) in toluene (100 mL) at 0° C. was added NaBr (Aldrich, 4.01 g, 40 mmole) in water (45 mL) followed by 2,2,6,6-tetramethyl-1-piperidinyloxy free radical (TEMPO reagent, Aldrich, 0.05 g, 0.32 mmole). To this vigorously-stirred mixture was added a mixture of Na$_2$CO$_3$ (11.16 g, 132 mmole)in water (50 mL) and aqueous NaOCl (0.7M, 65 mL, 46 mmole) dropwise over 30 minutes. After stirring 30 minutes at 0° C. the mixture was extracted with ethyl acetate (2×250 mL). The combined organics were washed with KI in 5% KHSO$_4$ (1×50 mL), then aqueous Na$_2$S$_2$O$_3$ (1×100 mL), then pH 7 phosphate buffer (1×100 mL), then brine (1×100 mL) and dried (Na$_2$SO$_4$). Filtration and evaporation of solvents left carbobenzyloxy-L-prolinal (5.55 g) as an oil.

23C. 1-(1-CBZ-2(S)-pyrrolidinyl)-1-buten-3-one

To a 350 mg (1.50 mmol) sample of CBZ-L-prolinal, from step 23b above, dissolved in 5 mL of methylene chloride was added 576 mg of 1-triphenylphosphoranylidene-2-propanone (Aldrich, 1.81 mmol). The reaction was stirred at room temperature for 45 min, then heated at reflux for 1.3 hr. The solution was cooled, and a precipitate formed. The mixture was extracted with methylene chloride (3×10 mL). The combined organics were washed with brine and dried over $MgSO_4$. The residue was chromatographed on silica gel, eluting with 25–35% ether in hexane. The title compound was isolated by removal of solvent (279 mg). Anal. Calcd for $C_{16}H_{19}NO_3$: C, 70.31; H, 7.01; N, 5.12; Found: C, 70.20; H, 7.02; N, 5.10.

23d. 1-(1-CBZ-2(S)-pyrrolidinyl)-1-buten-3-one oxime

A 250 mg (0.91 mmol) sample of the product from step 23c above was dissolved in 3 mL of pyridine, and 80 mg of hydroxylamine hydrochloride was added. The reaction was stirred for 2 hr, an additional 200 mg of hydroxylamine HCl was added, and the reaction stirred for another hour. The solvent was removed under vacuum, and the residue was partitioned between ether and water. The ether layer was washed with water, treated with solid $CuSO_4$, washed with brine, dried over $MgSO_4$ and concentrated. The residue was chromatographed on silica gel, eluting with 30% ethyl acetate in hexane, and 256 mg of the title compound was obtained after removal of solvent.

23e. 3-Methyl-5-(1-CBZ-2(S)-pyrrolidinyl)isoxazole

A 169 mg sample (0.59 mmol) of the product from step 23d above, 344 mg (2.07 mmol) of KI, 156 mg ((0.61 mmol) of $I_2$, and 198 mg (2.36 mmol) of $NaHCO_3$ were dissolved in 3 mL of water and 3 mL of THF. The mixture was heated at reflux for 6 hr, then cooled to room temperature. The mixture was diluted with 20 mL of 1.7M $NaHSO_3$ solution, then extracted with ether. The combined extracts were washed with brine and dried over $MgSO_4$, then concentrated to give 143 mg of crude product. Chromatography on silica gel, eluting with 20% ethyl acetate in hexane afforded 102 mg of the title compound after removal of the solvent.

23f. 3-Methyl-5-(1-methyl-2(S)-pyrrolidinyl)isoxazole

The Cbz-protected compound of step 23d is reacted with LAH in THF at 0° C. as described in Example 24 below, and the title compound is isolated in pure form by extraction with ethyl acetate and distillation under high vacuum.

EXAMPLE 24

Alternate Preparation Of 3-Methyl-5-(1-methyl-2(S)-pyrrolidinyl)isoxazole By the Procedure of Example 23

24a. N-Cbz-L-proline

L-Proline (10 g, 86.6 mmol) was dissolved in 66 mL of 2N NaOH and cooled to 0° C. To this solution were slowly and simultaneously added 34.35 mL of a solution of phenyl chloroformate in toluene (104.2 mmol) and 33 mL of 4N NaOH, over a period of 1 hr, while maintaining the reaction temperature at 0° C. and the pH above 7. After all reactants were added, the reaction was stirred for 6 hr at room temperature. The solution was then extracted with ether. The remaining aqueous layer was neutralized to pH 6–7 with 1N HCl, then extracted with ethyl acetate. The extract was dried over $Na_2SO_4$ and concentrated to afford 21.19 g of the title product (98% yield). $^1$H NMR ($CDCl_3$) δδ:9.55 (d, 1H), 7.3 (s, 5H), 5.25 (d, 2H), 4.35 (t, 1H), 4.20 (t, 1H), 1.8–2.2 (m, 4H).

24b. N-Cbz-L-prolinol

A 21.56 g (86.55 mmol) sample of the compound from step 248 above was dissolved in 200 mL of THF, and the solution was cooled to 0° C. $BH_3$-dimethyl sulfide (86.5 mL, 2N) was added dropwise under a nitrogen atmosphere. The reaction was stirred at room temperature for 16 hr, then cooled to 0° C. and quenched by careful addition of 10% acetic acid in methanol. The mixture was reduced in volume on a rotary evaporator, and the concentrate was dissolved in ethyl acetate, which was washed successively with 1N HCl, water and sodium bicarbonate solution. The organic extract was dried over $Na_2SO_4$ and concentrated to afford the title product, 19.94 g (98% yield).

24c. Alternate preparation Of N-Obz-L-prolinol

To a stirred suspension of sodium borohydride (7.59 g, 200 mmol) in 100 mL of THF cooled to 0° C. was added a solution of 20 g (80.28 mmol) of N-Cbz-L-proline, from step 24a above, in 50 mL of ether. To this solution was added dropwise a solution of 5 mL of $H_2SO_4$ in 20 mL of ether, with stirring and while maintaining the temperature below 20° C. The reaction mixture was warmed to room temperature and stirred for 16 hr. The reaction was quenched by the addition of 100 mL of methanol dropwise. The solvents were removed, 30 mL of 4N NaOH was added, and the mixture was extracted with ethyl acetate. The organic extract was dried over $Na_2SO_4$ and concentrated to afford the title product, 16.61 g (88 % yield).

24d. N-(Cbz-L-prolinal

To a stirred solution of N-Cbz-L-prolinol (5 g, 21.26 mmol, from steps 24b or 24c above) in 20 mL of anhydrous DMSO were added 8.89 mL (63.79 mmol) of triethylamine and 10.75 g (63.79 mmol) of $SO_3$-pyridine complex in 35 mL of DMSO. The reaction mixture was stirred at room temperature for 10 min, then poured into 200 mL of ice water. The mixture was extracted with ether, the extract was dried over $Na_2SO_4$ and concentrated to afford the title product, 3.058 g (70% yield).

24e. 1-(N-Cbz-2-pyrrolidinyl)-1-buten-3-one

To a stirred solution of N-Cbz-L-prolinal (6.3 g, 27 mmol, from step 24d above) in 30 mL of benzene was added 9.42 g (29.6 mmol) of 1-triphenylphosphoranylidene-2-propanone (Aldrich) at room temperature. The reaction mixture was heated to reflux for 4 hr. The benzene was removed under vacuum, and the residue was dissolved in ether and cooled for 16 hr. The phosphine oxide by product was removed by filtration, and the solution was further purified by column chromatography on silica gel, eluting with 20% ethyl acetate in hexanes, to afford 4.4 g of the title product (69% yield).

24f. 1-(N-Obz-2-pyrrolidinyl)-1-buten-3-ene oxime

To a stirred solution of the compound from step 24e above (5.29 g, 19.3 mmol) in 30 mL of methanol were added, in small portions, 1.34 g (19.36 mmol) of hydroxylamine HCl and 1.59 g (19.36 mmol) of sodium acetate. The reaction mixture was stirred at room temperature for 1 hr, then the solvent was removed. The residue was suspended in 30 mL of water and extracted with ether. The extract was dried over $Na_2SO_4$ and concentrated to afford the title product as a syrup (5.34 g, 96% yield). IR 3328, 3030, 2880, 1685, 1444, 1415, 1303, 1181, 1115, 1021,937 $cm^{-1}$.

24 g. 5-(1-Cbz-2(S)-pyrrolidinyl)-3-methylisoxazole

To a stirred solution of 6 g (20.83 mmol) of the oxime compound from step 24f above, in a wrapped flask to protect from light, was added 12.1 g (72.92 mmol) of KI dissolved in 80 mL of water and, in small portions, 7 g (83.33 mmol) of $NaHCO_3$ and 15.86 g (62.5 mmol) of iodine. The reaction was heated at reflux for 16 hr, cooled and diluted with saturated aq. $NaHSO_3$. The solution was extracted with ether, and the extract was washed with saturated aq. NaHSO$_3$, dried over Na$_2$SO$_4$, and concentrated to afford the title product (5.06 g, 85% yield). The compound was taken to the next step without further purification. IR 1702, 1604, 1444, 1417, 1356, 1173, 1103, 1079 cm$^{-1}$.

24h. 3-Methyl-5-(1methyl-2(S)-pyrrolidinyl)isoxazole

To a stirred solution of the Cbz-protected compound for step 24 g (5.3 g, 18.53 mmol) in 30 mL of THF cooled to 0° C. was added 1.463 g (37.06 mmol) of lithium aluminum hydride in small portions, and the mixture was stirred for 15 min. The reaction was quenched by adding aq. saturated Na$_2$SO$_4$. The mixture was extracted with ethyl acetate, and the solvent was concentrated. The crude residue was dissolved in dilute HCl (1N, 30 mL) and washed with ethyl acetate. The aqueous layer was neutralized with sodium bicarbonate solution, then extracted with ethyl acetate. The organic extract was dried over Na$_2$SO$_4$ and concentrated under vacuum the residue was purified by distillation under high vacuum to afford 1.51 g (43.7% yield). MS: 167 (M+H)$^+$, 184 (M+NH$_4$)$^+$. The e.e., analytical data, and NMR spectra agree with that of the product from Example 1 above. [α]$_D$=−106.19 (c=0.97, methanol).

EXAMPLE 25

Preparation of 3-Methyl-5-(1-methyl-2(S)-pyrrolidinyl) isoxazole Via N-(1-methylethylidine)isopropanamine 25a. N-(1-methylethylidine)isopropanamine Acetone ((116 g, 2.0 mol) and isopropylamine (118 g, 2.0 mol) were combined in a 500 mL round-bottom flask. The solution was stirred magnetically as concentrated HCl (1.0 g) was added dropwise. Stirring was continued under a reflux condenser with a drying tube during a a mildly exothermic reaction period. After 20 hr, solid NaOH (40 g, 1 mol) was added, and the mixture was stirred for 30 min. The solids were removed by filtration, and the filtrate was separated. The organic layer was distilled to remove isopropylamine and acetone and obtain the imine as a colorless liquid (98.0 g, 49% yield) b.p. 88°–90° C. $^1$H NMR (CDCl$_3$) δ: 1.11 (d, J=6.3 Hz, 6H), 1.83 (s, 3H), 3.59 (hept, J=6.3 Hz, 1H).

25b. 2-(1-methylethylidine)isopropanaminol-oxo-2-butenyl)-1-methylpyrrolidine

A solution of diisopropylamine (5.01 g, 49.6 mmmol) and N-(1-methylethylidine)isopropanamine (5.52 g, 55.7 mmol) in dry THF (60 mL) was prepared. The solution was stirred under nitrogen at −5°≠3° C. (ice-methanol bath) as n-butyllithiu/hexane (60 mL, 1.70M, 102 mmol) was added over a 20 min period. The solution was stirred for 1 hr at −5° C. A solution of N-methylproline methyl ester (7.16 g, 50.0 mmol) in 10 mL of THF was added over a 20 min period, while maintaining the temperature below 5° C. The solution was stirred at 0° C. for 90 min, then the reaction was quenched by the rapid addition of satd aq. NH$_4$Cl (40 g). The mixture was warmed to room temperature, and the layers were separated. The aqueous phase was extracted with ethyl acetate, the organic layers were combined, and the solution was dried over Na$_2$SO$_4$, filtered and concentrated under vacuum to give 10.5 g of an oil, which was taken directly to the next step. A pure sample for analysis was obtained upon distillation. b.p. 104°–110° C./0/40 mm Hg. $^1$H NMR (CDCl$_3$) δ:1.25 (d, J=7.0 Hz, 6 H), 1.68–1.92 (m, 3H), 2.01 (s, 3H), 2.01 (m, 1H), 2.21 (m, 1H), 2.34 (s, 3H), 2.63 (t, J= 7.9 Hz, 1H), 3.12 (m, 1H), 3.53 (d hept, J=2.4, 7.9 Hz, 1H), 5.21 (s, 1H), 11.02 (br, 1H).

25c. 4,5-dihydro-3-methyl-5-(1-methylpyrrolidin-2-yl)isoxazol-5-ol

The compound from step 25b above, 10.5 g) was dissolved in 20 mL of water and 20 mL of 25% (w/v) aqueous H$_2$SO$_4$. The solution was stirred at room temperature as 50% aqueous hydroxylamine (7.8 g, 118 mmol) was added. The pH was adjusted by addition of 25% H$_2$SO$_4$ to pH 5–6. The solution was stirred for 3 hr, then taken ,directly to the next step. For analytical purposes a sample was obtained by extracting an aliquot made basic by addition of 50% NaOH, extraction with ethyl acetate, and concentration under vacuum. $^1$H NMR (CDCl$_3$) δ:1.57–1.85 (m, 3H), 2.02 (t, J=1 Hz, 3H), 2.05 (m, 1H), 2.47 (m, 1H), 2.57 (s, 3H), 2.75 (dd, J=2.4, 7.9 Hz, 1H), 5.21 (s, 1H), 11.02 (br, 1H).

25d. 3-Methyl-5-(1-methyl-2(S)-pyrrolidinyl)isoxazole

To the solution of the product from step 25c above was added 12 mL of conc H$_2$SO$_4$, and the mixture was warmed to 70° C. and stirred for 2 hr. The solution was cooled in an ice-water bath, and adjusted to pH 12 by slow addition of 50% aqueous NaOH (40 g). The mixture was extracted twice with ethyl acetate, and the combined extracts were dried over Na$_2$SO$_4$. The solid were removed by filtration, and the filtrate was distilled, first at atmospheric pressure to remove the solvent and, finally, under vacuum to provide the title compound as a nearly colorless liquid (4.74 g, 57%). b.p. 115°–117° C./20 mm Hg. $^1$H NMR (CDCl$_3$) δ:1.8–2.1 (m, 3H), 2.32 (s, 3H), 2.21 (m, 1H), 2.29 (s, 3H), 2.36 (m, 1H), 3.17 (m, 1H), 3.53 (t, J=8 Hz, 1H), 6.01 (s, 1H).

What is claimed is:

1. The compounds, 5(S)-(3-methyl-5-isoxazolyl)-2-pyrrolidinone, 3-methyl-5-(1-methyl-2-pyrrolidinyl)-5-hydroxy-4,5-dihydro-isoxazole, and 1-(1-methyl-2(S)-pyrrolidinyl)-1,3-butanedione-3-oxime.

* * * * *

UNITED STATES PATENT AND TRADEMARK OFFICE
CERTIFICATE OF CORRECTION

PATENT NO. : 5,508,418         Page 1 of 3
DATED : April 16, 1996
INVENTOR(S) : N.H. Lin, et. Al.

It is certified that error appears in the above-indentified patent and that said Letters Patent is hereby corrected as shown below:

Column 1, line 3, change "C1-C3" to --$C_1$-$C_3$--.

Column 1, line 17-18, change "pyrrolidinyl-)" to --pyrrolidinyl)- --.

Column 1, line 45, change "betaketo" to --beta-keto--.

Column 3, line 65-66, change "simultaneous," to --simultaneous--.

Column 5, line 31, change "methylethylicline" to --methylethylidine--.

Column 12, line 40, change "(3-methyl" to --(3-methyl--.

Column 12, line 44, change "6.19" to --6.09--.

Column 15, line 14, change "Lame" to --Large--.

Column 15, line 18, change "2.:2" to --2.2--.

Column 15, line 22, change "4..34" to --4.34--.

UNITED STATES PATENT AND TRADEMARK OFFICE
CERTIFICATE OF CORRECTION

PATENT NO. : 5,508,418  
DATED : April 16, 1996  
INVENTOR(S) : N.H. Lin, et. Al.

Page 2 of 3

It is certified that error appears in the above-indentified patent and that said Letters Patent is hereby corrected as shown below:

Column 15, line 34, change "(2.61)" to --(2.6 L)--.

Column 16, line 49-50, insert --Example 9-- before the sentence beginning with "Another Preparation".

Column 16, line 61, change "temperature;" to --temperature--.

Column 18, line 1, change "methyl-,5" to --methyl-5--.

Column 19, line 19, change "diisopropylamine" to --diisopropylamine--.

Column 20, line 64, change "pyroglutamic" to --pyroglutamic--.

Column 24, line 2, change "248" to --24a--.

UNITED STATES PATENT AND TRADEMARK OFFICE
CERTIFICATE OF CORRECTION

PATENT NO. : 5,508,418
DATED : April 16, 1996
INVENTOR(S) : N.H. Lin, et al.

It is certified that error appears in the above-indentified patent and that said Letters Patent is hereby corrected as shown below:

Column 24, line 27, change "N-(Cbz-L-prolinal" to --N-Cbz-L-prolinal--.

Column 24, line 49, change "ene" to --one--.

Column 25, line 43, change "isopropanaminol" to --isopropanamin 0-1--.

Signed and Sealed this

Thirty-first Day of December, 1996

Attest:

BRUCE LEHMAN

*Attesting Officer*       *Commissioner of Patents and Trademarks*